(12) United States Patent
Nardi

(10) Patent No.: US 6,250,331 B1
(45) Date of Patent: Jun. 26, 2001

(54) ZERO CRACK-PRESSURE, HIGH-FLOW VALVE

(75) Inventor: Steven M. Nardi, Taunton, MA (US)

(73) Assignee: Haemonetics, Corp., Braintree, MA (US)

( * ) Notice: Subject to any disclaimer, the term of this patent is extended or adjusted under 35 U.S.C. 154(b) by 0 days.

(21) Appl. No.: 09/253,850

(22) Filed: Feb. 22, 1999

(51) Int. Cl.[7] .................................................. F16K 15/14
(52) U.S. Cl. .................... 137/517; 137/247.11; 137/248; 137/519; 137/859
(58) Field of Search ................... 137/517, 519, 137/859, 246, 247.11, 248

(56) References Cited

U.S. PATENT DOCUMENTS

| | | | |
|---|---|---|---|
| 3,286,728 | * 11/1966 | Stephenson | 137/856 |
| 4,045,009 | 8/1977 | Pees | 267/139 |
| 4,244,379 | 1/1981 | Smith | 128/766 |
| 4,523,610 | * 6/1985 | Orrico | 137/517 |
| 4,904,236 | 2/1990 | Redmond et al. | 604/9 |
| 4,986,310 | 1/1991 | Bailey et al. | 137/859 |
| 5,076,322 | 12/1991 | Choksi et al. | 137/505.13 |
| 5,520,632 | 5/1996 | Leveen et al. | 604/9 |
| 5,634,893 | 6/1997 | Rishton | 604/4 |
| 5,692,539 | * 12/1997 | Pickl, Jr. | 137/543.19 |
| 5,727,594 | 3/1998 | Choksi | 137/859 |
| 5,771,935 | 6/1998 | Myers | 137/859 |
| 5,830,172 | 11/1998 | Leveen et al. | 604/9 |
| 6,062,247 | * 5/2000 | King, Sr. | 137/517 |

* cited by examiner

Primary Examiner—John Rivell
Assistant Examiner—Ramesh Krishnamurthy
(74) Attorney, Agent, or Firm—Cesari & McKenna LLP

(57) ABSTRACT

The present invention is directed to a zero crack-pressure, high-flow valve assembly especially suited for use with blood salvage or recovery systems. The valve assembly cooperates with a valve seat defining an opening for selectively providing fluid communication between two adjacent chambers based on a pressure differential between the chambers. The valve assembly includes a disk coupled to a concentric ring support by a plurality of flexible or elastic arms, thereby permitting the disk to move relative to the ring support in a direction that is generally perpendicular to the plane of the ring support and the disk. The connecting arms also define fluid flow passages between the disk and ring support. The valve assembly is mounted so that the disk is normally spaced-apart from the valve seat, allowing fluid to flow between the two chambers. By increasing the relative pressure of the downstream chamber, the disk closes against the valve seat, blocking the opening.

26 Claims, 3 Drawing Sheets

ZERO CRACK-PRESSURE, HIGH-FLOW VALVE

CROSS-RELATED APPLICATIONS

This application is related to U.S. Pat. No. 5,634,893 entitled AUTOTRANSFUSION APPARATUS issued Jun. 3, 1997, and assigned to the assignee of the present application.

FIELD OF THE INVENTION

This invention relates to shed blood recovery systems, and more specifically, to a zero crack-pressure, high-flow valve especially suited for such systems.

BACKGROUND OF THE INVENTION

During surgical operations, patients often lose a significant amount of blood. To avoid serious complications, this blood volume is often replaced. In particular, whole blood or a blood component is transfused into the patient. To maintain adequate supplies of blood and blood components, many hospitals and blood banks rely on donors who are typically un-related to the transfusion recipients. Despite rigorous testing protocols, there remains some risk of transmitting blood-borne diseases during transfusions. Thus, it is desirable to limit or even avoid, if possible, transfusions of donated blood. One way of reducing the reliance on donated blood is to collect the patient's own blood that is shed during surgery. This blood may then be processed by a blood recovery system and re-infused into the patient. By salvaging a patient's own blood, one can limit the amount of donated blood that the patient must receive, thereby reducing the risk of exposure to blood-borne diseases.

U.S. Pat. No. 5,634,893, for example, is directed to an autotransfusion system that recovers shed blood. FIG. 1 is a block diagram of the '893 system 10. The system 10 includes a compound reservoir 12 having upper 16 and lower 14 chambers that are interconnected by a drain valve 18. A suction tube 22 connects a wound or surgical site to the upper chamber 16 which is also connected to a vacuum source 32. A selector valve 38 selectively couples the lower chamber 14 to the vacuum source 32 or to atmospheric pressure. Normally, the valve 38 is positioned so that the vacuum is applied equally to both chambers 14, 16. That is, the absolute pressure in both chambers 14, 16 is the same. Accordingly, blood from the surgical site is drawn through suction tube 22 and into the upper chamber 16. The blood first flows through a particle filter 20 located in the upper chamber 16 to remove debris, such as blood clots, bone chips, etc. The filtered blood then collects in the upper chamber 16. A lipid (i.e., liquid oils) separation system 61 is also located in the upper chamber 16. The lipid separator 61 includes a partition 60 having an opening 60a, a dam 64 and moat 62 that are formed around the drain valve 18 and cooperate to block lipids from flowing through the drain valve 18 and entering the lower chamber 14. Thus, the shed blood that drains into the lower chamber 14 is substantially free of particles and lipids.

The drain valve 18 located between the two chambers 14, 16 is a conventional, vacuum-operated, duckbill-type drain valve. That is, drain valve 18 includes a pair of opposing lips 80a, 80b that are formed from a flexible or elastomeric material. The two lips 80a, 80b are normally sealed at their outer ends 82a, 82b but may be opened to define an aperture. That is, the ends 82a, 82b of the two opposing lips 80a, 80b are normally in contact with each other, thereby blocking the flow of fluid between the two chambers 14, 16. When a sufficient volume of filtered, lipid-reduced blood builds-up within the drain valve 18, the corresponding fluid pressure exerted on the inside of the flexible lips 80a, 80b causes them to open and allow the blood to flow through the aperture defined thereby and enter the lower chamber 14.

When the lower chamber 14 is full of blood or contains a sufficient volume for reinfusion, the selector valve 38 is moved to the second position, thereby venting the lower chamber 14 to atmospheric pressure. The upper chamber 16 nonetheless remains at vacuum pressure. The pressure differential between the two chambers 14, 16 causes the two lips 80a, 80b of the drain valve 18 to close together, stopping the flow of blood between the two chambers 14, 16, and also preventing vacuum loss in upper chamber 14. The blood in the lower chamber 16 may then be drained to a blood bag 76 for subsequent transfusion. Once the lower chamber 16 has been emptied, the blood bag 76 is sealed-off by a clamp 74 and the selector valve 38 is returned to the first position, allowing filtered, lipid-reduced blood to drain into the lower chamber 14, as described above.

As shown, the '893 system allows processed, recovered blood to be transferred to a blood bag without interrupting the suction being applied to the surgical site. Thus, the '893 system efficiently salvages shed blood without disrupting the drainage of surgical sites. It has been discovered, however, that the duckbill-type drain valve has several disadvantages. First, as described above, the valve is normally in a closed position. That is, the two opposing lips are normally in contact at their outer ends and are only opened in response to fluid pressure exerted by a volume of blood inside the valve. The valve, moreover, is formed from bio-compatible silicone whose physical properties, unlike certain metals and hard plastics, can vary greatly, even if the silicone is manufactured by the same supplier under generally the same conditions. Accordingly, the fluid pressure required to "crack" or break open the prior art valve can vary significantly from one valve to the next. In some instances, the crack pressure may actually exceed the fluid pressure that can practically be generated within the blood recovery system (e.g., the column of blood necessary to open the valve exceeds the height of the upper chamber). This lack of predictability in the crack pressure of the prior art valve raises significant quality assurance issues.

Additionally, sterilization of the '893 system can result in the valve becoming sealed, effectively preventing it from opening at all. More specifically, during sterilization, the '893 blood recovery system, including the duckbill valve, is typically heated to approximately 60° C. At this temperature, the surface of silicone components often becomes "tacky". If two of these "tacky" surfaces are brought into contact with each other, they can adhere to one another. Since the conventional duckbill valve has two silicone lips that are in contact with each other, sterilization can cause the two surfaces to adhere to each other, significantly increasing the force needed to open the valve. Indeed, the volume of fluid required to open the valve may actually exceed the capabilities of the '893 system. Sterilization can thus render the conventional valve inoperable.

Accordingly, a need has arisen for a new valve assembly that preferably opens at zero fluid pressure (e.g., a zero crack-pressure valve), but provides a relatively high fluid flowrate. It is an object of the present invention to provide a valve assembly having zero crack pressure and a high flowrate. It is a further object of the present invention to provide a valve that does not degrade or become inoperable following sterilization. Another object of the present invention is provide a valve that reliably and predictably opens and closes. A further object of the present invention is to provide a valve that closes in response to slight pressure differentials across the valve.

SUMMARY OF THE INVENTION

Briefly, the present invention relates to a zero crack-pressure, high-flow valve assembly especially suited for use with blood salvage or recovery systems. The valve assembly cooperates with a valve seat defining an opening for selectively providing fluid communication between two adjacent chambers based on the pressure differential between the chambers. The valve assembly includes a disk that is slightly larger than the opening in the valve seat. One or more flexible or elastic arms connect the disk to a concentric ring support permitting the disk to move relative to the ring support in a direction that is generally perpendicular to the nominal plane of the ring support. The connecting arms also define fluid flow passages between the disk and ring support. The valve assembly is mounted so that the disk is adjacent to and downstream of the opening in the valve seat. That is, the disk is normally spaced-apart from the valve seat. The valve assembly may be secured to one of the chambers by means of a valve cap.

The connecting arms allow the disk to move between a normally open position (where the disk is spaced-apart from the valve seat, thereby allowing fluid communication between the two chambers) and a closed position (where the disk is pushed against the valve seat, blocking the opening and suspending fluid communication). The disk of the valve assembly remains in the open position provided that the absolute pressure in the two chambers is equalized (or the upstream chamber is at higher absolute pressure). Thus, no (i.e., zero) fluid pressure is required to crack or break open the valve assembly. To close the valve, the absolute pressure in the downstream chamber is increased relative to the upstream chamber. This pressure differential drives the disk against the valve seat, blocking the opening and preventing fluid from flowing between the two chambers. In the preferred embodiment, the disk is spaced from the opening such that an annular fluid ring forms between the disk and the opening as fluid drains into the downstream chamber. The presence of the annular fluid ring facilitates closure of the valve assembly at extremely low pressure differentials between the two chambers.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
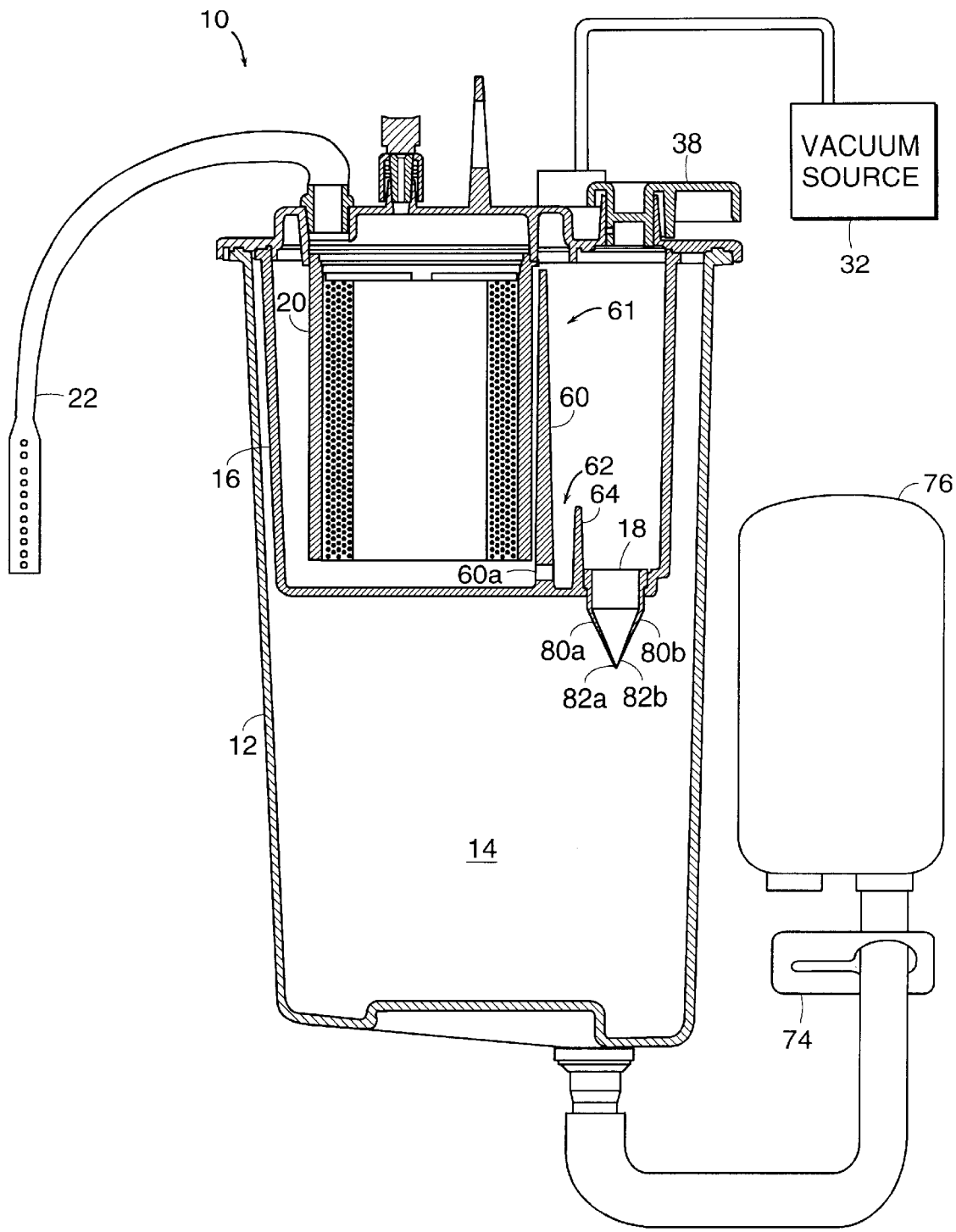
FIG. 1, previously discussed, is a cross-sectional side view of the prior art blood recovery system.
Figure 2:
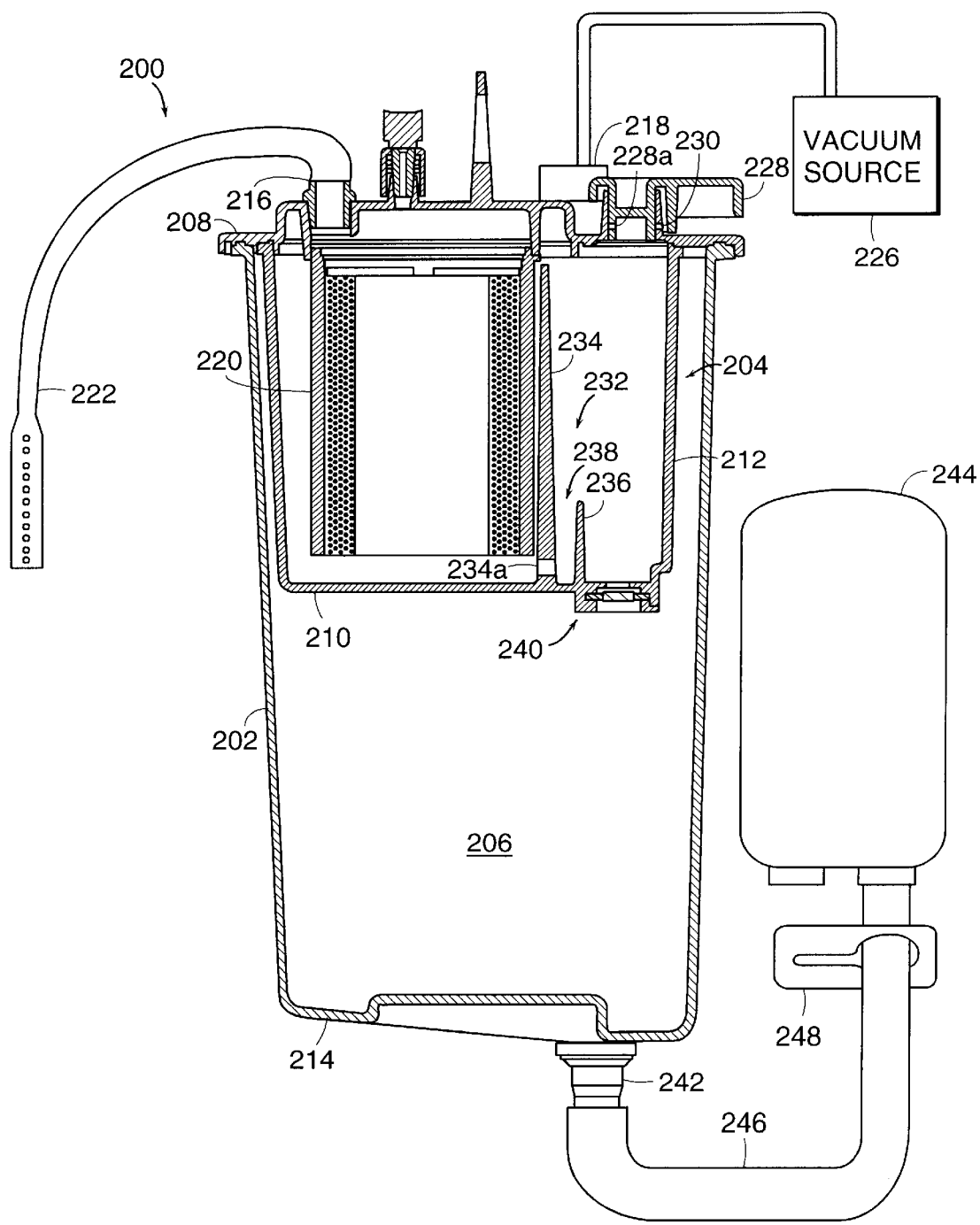
FIG. 2 is a cross-sectional side view of a blood recovery system in accordance with the present invention.

FIG. 2 is a cross-sectional view of a blood recovery system 200. The system 200 includes a compound reservoir 202 having an upper chamber 204, a lower chamber 206 and a cover 208. The upper chamber 204, which is sealingly engaged to the cover 208, includes a base 210 and a generally cylindrical side wall 212. The reservoir 202 also includes a base 214 which is located in the lower chamber 206. Extending through the cover 208 is a blood inlet port 216 and a vacuum port 218. A particle filter 220 is disposed in the upper chamber 204 for receiving blood from the blood inlet port 216. A suction tube 222 for suctioning blood from a wound or surgical site is coupled to the blood inlet port 216 of the upper chamber 204. A vacuum source 226 for creating a vacuum in the upper chamber 204 is coupled to the vacuum port 218 in the cover 208. Also mounted on the cover 208 of the reservoir 202 are a selector valve 228 and an atmospheric vent 230. The atmospheric vent 230 may be formed in an inner support housing for the selector valve 228. It should be understood that other components, such as auxiliary connectors, negative pressure relief valves, etc. (not shown), may be located in the cover 208.

The selector valve 228 is capable of selectively coupling the lower chamber 206 of the reservoir 202 either to the vacuum source 226 or to the atmospheric vent 230. More specifically, the selector valve 228, which is moveable between first and second positions, includes a port 228a that can be selectively placed in fluid communication with either the vacuum port 218 or the atmospheric vent 230. In the first position, the port 228a of the selector valve 228 couples the vacuum source 226 to the lower chamber 206 is by way of the vacuum port 218. In the second position, the port 228a of the selector valve 228 couples the lower chamber 206 to the atmospheric vent 230. A lipid separation system 232 is located in the upper chamber 204. The lipid separation system 232 includes a partition 234 having an aperture 234a, and a dam 236. The dam 236 is spaced from the partition 234 by a moat 238. The dam 236, moreover, surrounds a zero crack-pressure, high-flow valve assembly 240 that is preferably disposed in the base 210 of the upper chamber 204 and configured to selectively provide fluid communication between the upper and lower chambers 204, 206.

A drain port 242 is located in the base 214 of the reservoir 202 in the lower chamber 206. A blood bag 244 for receiving processed, salvaged blood from the system 200 is coupled to the drain port 242 by a drain tube 246. A moveable clamp 248 is preferably attached to the drain tube 246. A suitable system for use with the present invention is described in U.S. Pat. No. 5,634,893, which is hereby incorporated by reference in its entirety.

Figure 3:
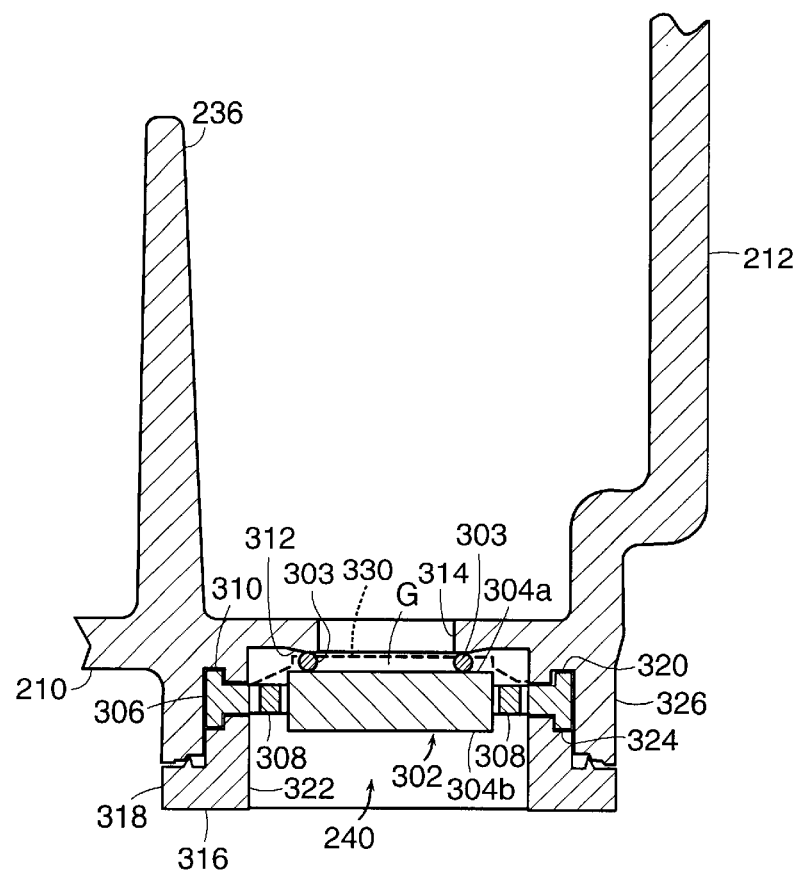
FIG. 3 is an enlarged cross-sectional view of the valve assembly of the blood recovery system of FIG. 2.

FIG. 3 is an enlarged cross-sectional view of the zero crack-pressure, high flow valve assembly 240 of FIG. 2. The valve assembly 240 includes a disk 302 having two opposing disk surfaces 304a, 304b. The valve assembly 240 further includes a ring support 306 that is concentrically disposed around the disk 302. One or more flexible arms 308 connect the disk 302 to the ring support 306 which includes an elongated outer rim 310. A valve seat 312 defining an opening 314 is formed in the base 210 of the upper chamber 204. The opening 314 provides fluid communication between the upper and lower chambers 204, 206 (FIG. 2). The disk 302 of the valve assembly 240 is preferably mounted adjacent to the valve seat 312 such that one of the disk surfaces (e.g., surface 304a) is spaced-apart from the valve seat 312 by a gap, G. In addition, the diameter of the disk 302 is preferably greater than the diameter of the opening 314, thereby defining an annular-shaped zone of contact (not shown) around the opening 314 in the valve seat 312. When the disk 302 is pressed against the valve seat 312, as described below, it engages the zone of contact.

The valve assembly 240 may be securely attached to the base 210 of the upper chamber 204 by a circular valve cap 316 having a shelf 318. In particular, the valve seat 312 may include a circular recess 320 that faces the lower chamber 206 (FIG. 2) and is concentrically disposed around the opening 314. The recess 320 is configured to receive one-half of the elongated rim 310 of the ring support 306. The valve cap 316 may include a flange 322 on the end opposite the shelf 318 that includes a cut-out 324 configured to receive the other half of the elongated rim 310. The valve seat 312 further includes a circular sleeve 326 concentrically disposed about the recess 320 that extends toward the lower chamber 206. The shelf 318 of the valve cap 316 preferably attaches to the end of the sleeve 326, thereby securing the valve assembly 240 in place.

Figure 4A:
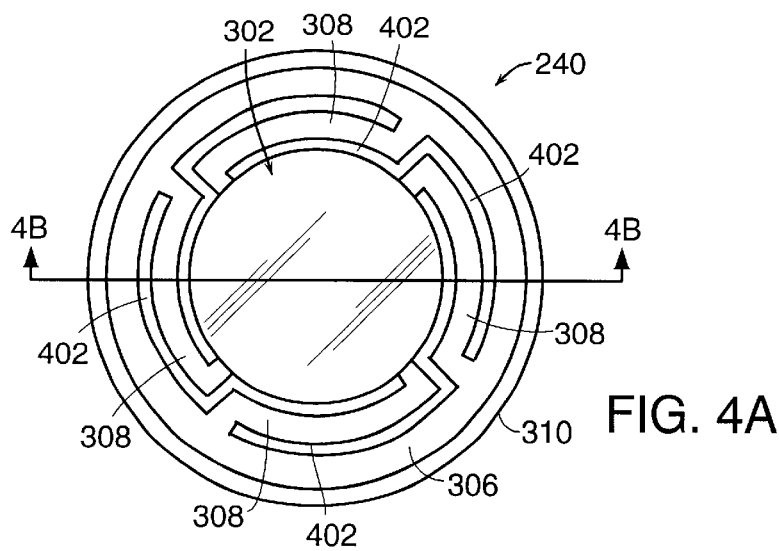
FIG. 4A is a top view of the valve assembly of the present invention.
Figure 4B:
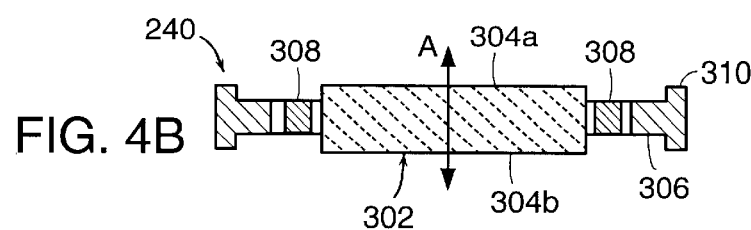
FIG. 4B is a side view of the valve assembly of FIG. 4A.

FIGS. 4A and 4B are top and side views, respectively of the valve assembly 240. As shown, the preferred valve assembly 240 includes four serpentine-shaped, flexible arms 308 that connect the disk 302 to the ring support 306. The connecting arms 308, moreover, define a plurality of slots 402 or openings between the disk 302 and the ring support 306. Arms 308 allow disk 302 to move perpendicular to the nominal plane of the ring support 306 as shown by arrow A (FIG. 4B). Due to the serpentine shape of connecting arms 308, disk 302 may also rotate slightly during movement along arrow A. Nonetheless, the connecting arms 308 are preferably configured to retain the disk 302 generally within the plane of the ring support 306 absent an external force acting on the disk 302. To provide stability to the valve assembly 240, the thickness of the disk 302 is preferably greater than the thickness of the connecting arms 308. The entire valve assembly 240, including the disk 302, flexible arms 308 and ring support 306, is preferably formed in one piece from bio-compatible silicone having a durometer of 30–40 on the Shore Type A durometer scale.

Operation of the system 200 is as follows. The end of the suction tube 222 is placed in the wound or surgical site. With the selector valve 228 placed in the first position, the vacuum generated by the vacuum source 226 is equally applied to both the upper and lower chambers 204, 206. That is, the absolute pressure in the two chambers 204, 206 is the same. The relative vacuum generated by vacuum source 226 is preferably between 25–100 mm of mercury (Hg). The presence of a vacuum in the upper chamber 204 draws blood from the site through the tube 222 and into the particle filter 220 which traps debris that is present in the blood. Filtered blood collects in the upper chamber 204 and flows through the aperture 234a in the partition 234 where it collects in the moat 238. Partition 234 prevents lipids in the filtered blood from flowing into the moat 238. When the blood within the moat 238 rises to the level of the dam 236, it spills over the dam 236 and flows toward the opening 314 (FIG. 3) in the valve seat 312.

With the pressure equalized between the two chambers 204, 206, the disk 302 of the valve assembly 240 remains spaced from the opening 314 in the valve seat 312 by the gap G. That is, the flexible connecting arms 308 are configured, as described above, to retain the disk 302 generally within the plane of the ring support 306. As a result, filtered, lipid-reduced blood flows through the opening 314 in the valve seat 312. The blood then flows across the upper surface 304a of the disk 302, through the slots 402 (FIG. 4A) defined by the connecting arms 308 and down into the lower chamber 206.

Blood continues to be withdrawn from the surgical site, processed in the upper chamber 204 and delivered to the lower chamber 206 until the lower chamber 206 is either filled with processed, salvaged blood or contains sufficient blood for re-infusion. At this point, the attendant preferably moves the selector valve 228 to the second position, thereby venting the lower chamber 206 to atmospheric pressure. With the vacuum source 226 still pulling a vacuum in the upper chamber 204, a pressure differential will exist between the upper and lower chambers 204, 206. This pressure differential drives the disk 302 in the direction of arrow A (FIG. 4B) toward the opening 314 until the upper surface 304a of the disk 302 contacts and engages the zone of contact at the valve seat 312, as shown in phantom outline 330 in FIG. 3. That is, the force exerted on the disk 302 as a result of the pressure differential between the two chambers 204, 206 overcomes the spring force of the connecting arms 308 and moves the disk 302 in the direction of arrow A until it engages the valve seat 312. With the disk 302 pressed against the valve seat 312, the opening 314 is blocked and the lower chamber 206 is sealed from the upper chamber 204. Accordingly, the flow of blood between the two chambers 204, 206 is suspended. Nonetheless, blood continues to drain from the wound to the upper chamber 204 which remains coupled to the vacuum source 226.

To facilitate closure of the valve assembly 240 at relatively low pressure differentials (e.g., 25 or 50 mm Hg pressure differential), the gap G is selected so that an annular fluid ring (303) forms and remains between the valve seat 312 and the disk 302, despite continued blood flow through the valve assembly 240. This annular ring essentially provides a vapor seal between the two chambers 204, 206, forcing the pressure differential to act on the disk 302. Without an annular fluid ring, small pressure differentials may only result in higher pressure air in the lower chamber 206 flowing around the disk 302 and into the upper chamber 204, rather than driving the disk 302 against the valve seat 312 and blocking the opening 314. In the preferred embodiment, the diameter of the opening 314 in the valve seat 312 is approximately 0.200 inches and the diameter of the disk 302 is approximately 0.312 inches. The gap G between the valve seat 312 and the disk 302 is on the order of 0.030 to 0.040 inches.

With the lower chamber 206 vented to atmospheric pressure, the filtered, lipidreduced blood may be transferred to the blood bag 244. In particular, the clamp 248 in the drain tube 246 may be moved to the open position, allowing blood from the lower chamber 206 to be gravity fed into the blood bag 244. When the lower chamber 206 is empty, the clamp 248 in the drain tube 246 is closed. The attendant then returns the selector valve 228 to the first position, thereby coupling the lower chamber 206 to the vacuum source 226 once again. With the absolute pressure in the two chambers 204, 206 equal, the spring force of the flexible connecting arms 308 moves the disk 302 away from the opening 314 in the valve seat 312. In particular, the connecting arms 308 return the disk 302 to the plane of the ring support 306, thereby allowing blood to flow between the two chambers 204, 206, as described above.

While the lower chamber 206 is vented to atmospheric pressure and blood is drained to the blood bag 244, a volume of filtered, lipid-reduced blood will accumulate on the upstream side of the valve assembly 240. This volume of blood exerts a fluid pressure head that facilitates the opening the valve assembly 240 when the absolute pressure in the two chambers 204, 206 is equalized. To further assist in the opening of the valve assembly 240, the area immediately around the opening 314 in the valve seat 312 is preferably raised. In addition, the zone of contact may be provided with a textured surface, thereby reducing the effective surface area that is in contact with the disk 302 when the valve assembly 240 is in the closed position. For example, the surface may be grooved or etched. The textured surface also facilitates opening of the valve assembly 240 and avoids adhesion of the disk 302 to the valve seat 312.

In addition, a column of filtered, lipid-reduced blood may form and remain on the upstream side of the valve assembly 240 while the pressure in the two chambers 204, 206 is equalized, and processed blood drains into the lower or downstream chamber 206. This fluid column exerts a pressure head on the valve assembly 240 displacing the disk 302 in the direction of arrow A away from the valve seat 312, and thus further opening the valve assembly 240. More specifically, with a durometer in the range of 30–40, the disk 302 may be displaced on the order of 0.040 inches. By further opening the valve assembly 240, the flowrate of filtered, lipid-reduced blood into the lower or downstream chamber 206 is increased.

As shown, the zero crack-pressure, high-flow valve assembly of the present invention provides several advantages over the prior art valve. In particular, the disk of the valve assembly is normally spaced from the opening in the valve seat. That is, the valve assembly of the present invention is normally in the open position, unlike the prior art valve which is normally in the closed position. Thus, the present invention provides fluid communication between the two chambers without the need for a fluid pressure head to build up ahead of the valve assembly. In addition, the valve assembly of the present invention avoids the adherency problems caused by having two silicone surfaces in contact with each other during sterilization. In the present invention, the silicone disk is not in contact with any other component during sterilization and thus does not adhere to any other components. Furthermore, the valve assembly of the present invention reliably opens upon equalization of the pressure in the two chambers. Indeed, although the disk of the present invention may become somewhat tacky following sterilization, the disk only contacts the valve seat of the upper chamber which is preferably formed from hard plastic such as polycarbonate. The disk does not contact another tacky silicone surface. In fact, once the disk is wet, which will normally occur before the valve assembly is ever closed, the likelihood of it adhering to the valve seat is significantly reduced. Thus, when the absolute pressure between the two chambers is equalized (or the upstream chamber is at higher absolute pressure), the valve assembly reliably opens every time. This is significant because the valve assembly of the blood recovery system may be cycled (i.e., opened and closed) many times during the recovery process.

The foregoing description has been directed to specific embodiments of this invention. It will be apparent, however, that other variations and modifications may be made to the described embodiments with the attainment of some or all of their advantages. In particular, those skilled in the art will recognize that the ring support 306 and connecting arms 308 cooperate to form a spring mount for moving the operative surface 304a of the disk 302 relative to the opening 314 in the valve seat 312. Other arrangements for forming a spring mount are also possible. For example, the ring support 306 may be omitted and the connecting arms 308 may be attached directly to the circular sleeve 326 of the valve seat 312. Alternatively, the connecting arms 308 may be omitted and the valve assembly 240 may include a thin, elastic membrane connecting the disk 302 to the ring support 306 with perforations in the rim 310 of the ring support 306 to allow fluid flow. Accordingly, this description should be taken only by way of example and not by way of limitation. It is the object of the appended claims to cover all such variations and modifications as come within the true spirit and scope of the invention.

What is claimed is:

1. A valve assembly for use with a valve seat that defines an opening between two chambers through which a liquid may flow, the valve assembly selectively providing or blocking fluid communication between the two chambers, the valve assembly comprising:
   a valve surface movably positionable adjacent to the opening in the valve seat; and
   a spring mount, connected to the valve surface, for moving the surface between
      (1) a first position in which the valve surface is in spaced-apart relation relative to the opening in the valve seat whenever the two chambers are at equal vapor pressure, and
      (2) a second position in which the valve surface engages the valve seat, thereby sealing the opening and blocking both liquid and vapor fluid communication between the two chambers in response to a vapor pressure differential between the two chambers,
   wherein
      in the first position, the valve surface and the valve seat cooperate such that a liquid fluid ring forms a vapor seal between the valve seat and the valve surface permitting the liquid but not the vapor to flow between the two chambers.

2. The valve assembly of claim 1 wherein the valve surface moves to the second position when the downstream chamber relative to the direction of fluid flow is at a higher absolute pressure than the upstream chamber.

3. The valve assembly of claim 2 wherein the valve surface has a diameter that is greater than the opening in the valve seat.

4. The valve assembly of claim 3 wherein the valve surface moves to the second position when the downstream chamber is at atmospheric pressure and the upstream chamber is at a vacuum pressure.

5. The valve assembly of claim 4 wherein, in the second position, the valve surface engages the valve seat about a zone of contact that is textured to reduce its surface area.

6. The valve assembly of claim 4 wherein the valve assembly is formed from biocompatible silicone having a durometer of 30–40 on the Shore Type A durometer scale.

7. The valve assembly of claim 6 wherein the valve surface is a surface of a disk.

8. The valve assembly of claim 7 wherein the spring mount comprises:
   a ring support concentrically disposed around the disk; and
   one or more flexible arms connecting the disk to the ring support, the one or more connecting arms defining at least one fluid flow slot between the disk and the ring support.

9. The valve assembly of claim 8 having a plurality of serpentine-shaped connecting arms extending between the ring support and the disk.

10. The valve assembly of claim 9 further comprising a valve cap that secures the valve assembly to the upstream chamber.

11. The valve assembly of claim 1 wherein the vapor seal facilitates the sealing of the opening in response to a vapor pressure differential between the two chambers.

12. The valve assembly of claim 11 wherein the vapor seal is formed by an annular fluid ring between the valve seat and the valve surface.

13. The valve assembly of claim 12 wherein the fluid flowing between the two chambers is blood and the spacing between the valve surface and the adjacent opening when the valve surface is in the first position is on the order of 0.030 to 0.040 inches.

14. The valve assembly of claim 1 wherein the valve surface is a surface of a disk and the spring mount comprises:
   a ring support concentrically disposed around the disk; and
   a plurality of flexible arms connecting the disk to the ring support, the connecting arms defining at least one fluid flow slot between the disk and the ring support.

15. The valve assembly of claim 14 wherein the at least one fluid flow slot increases in area as the disk moves away from the opening in the valve seat.

16. The valve assembly of claim 14 wherein each arm defines a pair of fluid flow slots between the disk and the ring support.

17. The valve assembly of claim 16 wherein each fluid flow slot increases in area as the disk moves away from the opening in the valve seat.

18. A method for selectively providing or blocking fluid communication between two chambers separated by a valve seat that defines an opening through which a liquid may flow, the method comprising the steps of:
   providing a movably positionable valve surface adjacent to the opening in the valve seat; and
   moving the valve surface between
      (1) a first position in which the valve surface is in spaced-apart relation relative to the opening in the valve seat whenever the two chambers are at equal vapor pressure, and
      (2) a second position in which the valve surface engages the valve seat, thereby sealing the opening and blocking fluid communication between the two chambers, in response to a vapor pressure differential between the two chambers,
   wherein
      in the first position, the valve surface and the valve seat cooperate such that a liquid fluid ring forms a vapor seal between the valve seat and the valve surface permitting the liquid but not the vapor to flow between the two chambers.

19. The method of claim 18 wherein the valve surface moves to the second position when the downstream chamber relative to the direction of fluid flow is at a higher absolute pressure than the upstream chamber.

20. The method of claim 18 further wherein the vapor seal between the valve seat and the valve surface facilitates the sealing of the opening in response to a vapor pressure differential between the two chambers.

21. The method of claim 20 wherein the vapor seal is formed by an annular fluid ring between the valve seat and the valve surface.

22. The method of claim 21 wherein the fluid flowing between the two chambers is blood and the spacing between the valve surface and the adjacent opening when the valve surface is in the first position is on the order of 0.030 to 0.040 inches.

23. The method of claim 18 further comprising the steps of:
   providing at least one fluid flow slot in the valve assembly, the at least one fluid flow slot having an area; and
   increasing the area of the at least one fluid flow slot as the valve surface moves away from the opening in the valve seat.

24. Apparatus for collecting and salvaging blood, the apparatus comprising:
   a first chamber for collecting blood;
   a second chamber in fluid communication with the first chamber for receiving blood therefrom;
   a vacuum port associated with the first chamber for coupling the first chamber to a vacuum source;
   a selector valve in fluid communication with the second chamber for alternatingly venting the second chamber or coupling the second chamber to the vacuum port; and
   a valve assembly for use with a valve seat that defines an opening between the two chambers through which blood may flow, the valve assembly selectively providing or blocking fluid communication between the two chambers, the valve assembly comprising:
      a valve surface movably positionable adjacent to the opening in the valve seat; and
      a spring mount, connected to the valve surface, for moving the surface between
         (1) a first position in which the valve surface is in spaced-apart relation relative to the opening in the valve seat whenever the two chambers are coupled to the vacuum source, and
         (2) a second position in which the valve surface engages the valve seat, thereby sealing the opening and blocking both liquid and vapor fluid communication between the two chambers in response to venting the second chamber,
   wherein
      in the first position, the valve surface and the valve seat cooperate such that a liquid fluid ring forms a vapor seal between the valve seat and the valve surface permitting liquid but not vapor communication between the two chambers.

25. The apparatus of claim 24 wherein the valve surface is a surface of a disk and the spring mount comprises:
   a ring support concentrically disposed around the disk; and
   a plurality of flexible arms connecting the disk to the ring support, the connecting arms defining at least one fluid flow slot between the disk and the ring support.

26. The apparatus of claim 25 wherein the at least one fluid flow slot increases in area as the disk moves away from the opening in the valve seat.

* * * * *